United States Patent [19]
Manning

[11] Patent Number: 5,640,735
[45] Date of Patent: Jun. 24, 1997

[54] TURBINE POWERED TOOTHBRUSH HAVING GEAR FLUSHING SYSTEM

[76] Inventor: Peter T. Manning, 330 Connaught, Houston, Tex. 77015

[21] Appl. No.: 363,635

[22] Filed: Dec. 21, 1994

Related U.S. Application Data

[63] Continuation-in-part of Ser. No. 264,428, Jun. 22, 1994, abandoned.

[51] Int. Cl.⁶ .................................................... A46B 13/06
[52] U.S. Cl. ............................ 15/29; 15/28; 601/162; 601/165
[58] Field of Search ........................... 15/29, 28, 22.1, 15/24, 97.1; 601/139, 141, 142, 114, 154, 162, 165, 160

[56] References Cited

U.S. PATENT DOCUMENTS

| | | | |
|---|---|---|---|
| 736,607 | 8/1903 | Lane | 15/29 |
| 1,691,523 | 11/1928 | Maycen | 15/29 |
| 2,140,307 | 12/1938 | Belaschk et al. | 15/28 |
| 3,509,874 | 5/1970 | Stillman | 15/28 |
| 3,869,746 | 3/1975 | Man-king | 15/29 |
| 4,282,623 | 8/1981 | Gacuzana | 15/29 |
| 5,153,962 | 10/1992 | Ritter | 15/29 |
| 5,465,445 | 11/1995 | Yeh | 15/29 |
| 5,500,973 | 3/1996 | Phelan | 15/29 |

FOREIGN PATENT DOCUMENTS

| | | | |
|---|---|---|---|
| 291368 | 11/1967 | Australia | 15/29 |
| 261422 | 4/1968 | Austria | 15/29 |
| 280833 | 9/1988 | European Pat. Off. | 15/29 |
| 478383 | 6/1929 | Germany | 15/29 |
| 303720 | 12/1932 | Italy | 15/29 |
| 512380 | 9/1955 | Italy | 15/24 |
| 2175494 | 12/1986 | United Kingdom | 15/29 |

*Primary Examiner*—Gary K. Graham
*Attorney, Agent, or Firm*—Bush, Riddle & Jackson, L.L.P.

[57] ABSTRACT

A power driven dental toothbrush mechanism is provided having a suitable power source such as a water turbine motor or an electric motor operating through a drive shaft and gear train assembly to accomplish controlled rotation of a plurality of gear driven bristle tufts. A brush head assembly is releasably connected to a motor housing structure and defines an internal gear chamber within which is located a plurality of bristle tuft gears and drive gears therefor. The toothbrush mechanism incorporates a flushing water supply passage in communication with a water inlet source and which transitions the joint between the brush head and housing structure and opens into the internal gear chamber. The brush head and housing structure also define a flushing water exhaust passage in communication with the internal gear chamber of the brush head opposite the flushing water inlet. The flushing water exhaust passage extends through the brush head and a portion of the housing structure and terminates at an exhaust port that is located on the housing structure in a position that is easily engaged by a finger of the user. The brush head is provided with a water outlet valve which is preferably a normally closed, pressure responsive valve that is opened when water pressure within the internal gear chamber is increased to a predetermined value by user placement of a finger over the flushing water outlet port.

14 Claims, 6 Drawing Sheets

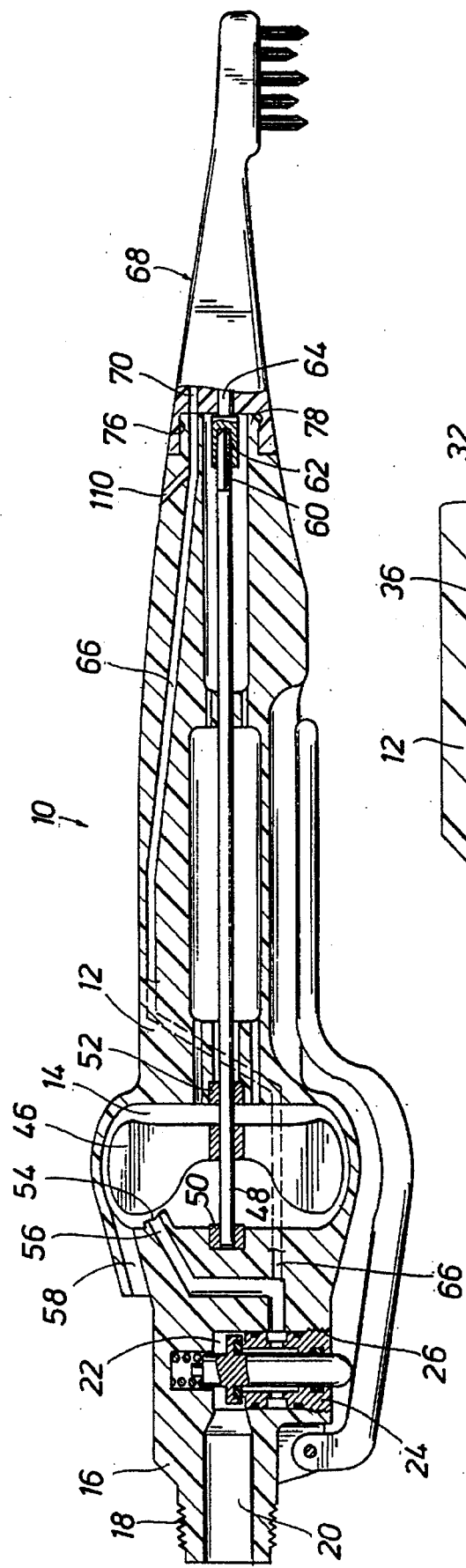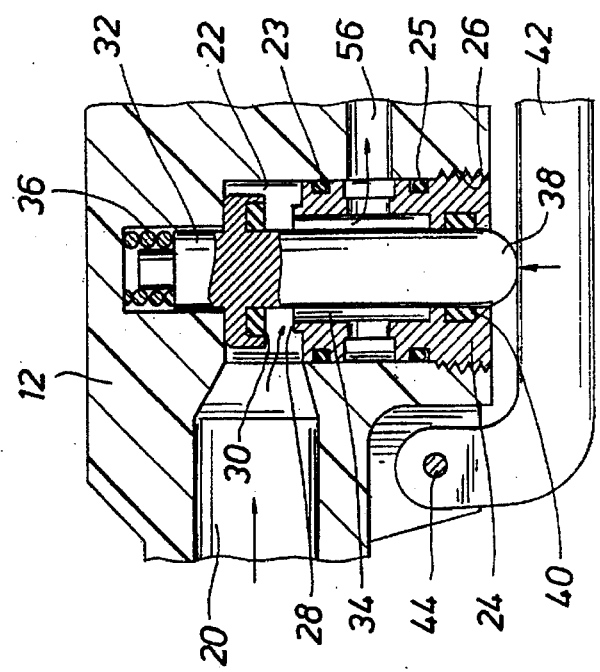

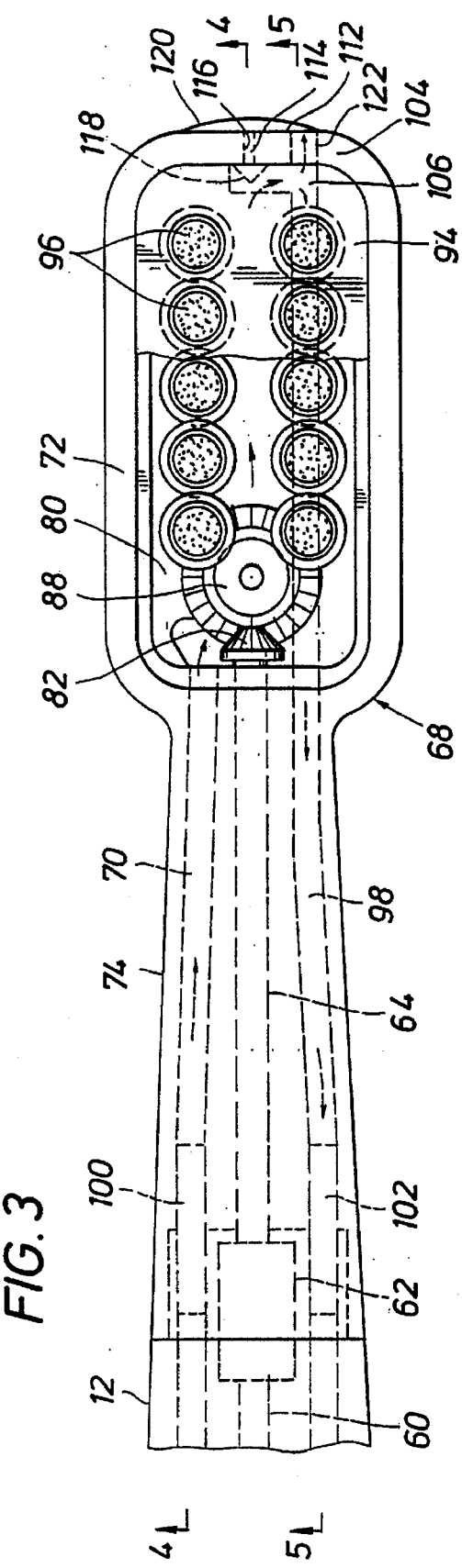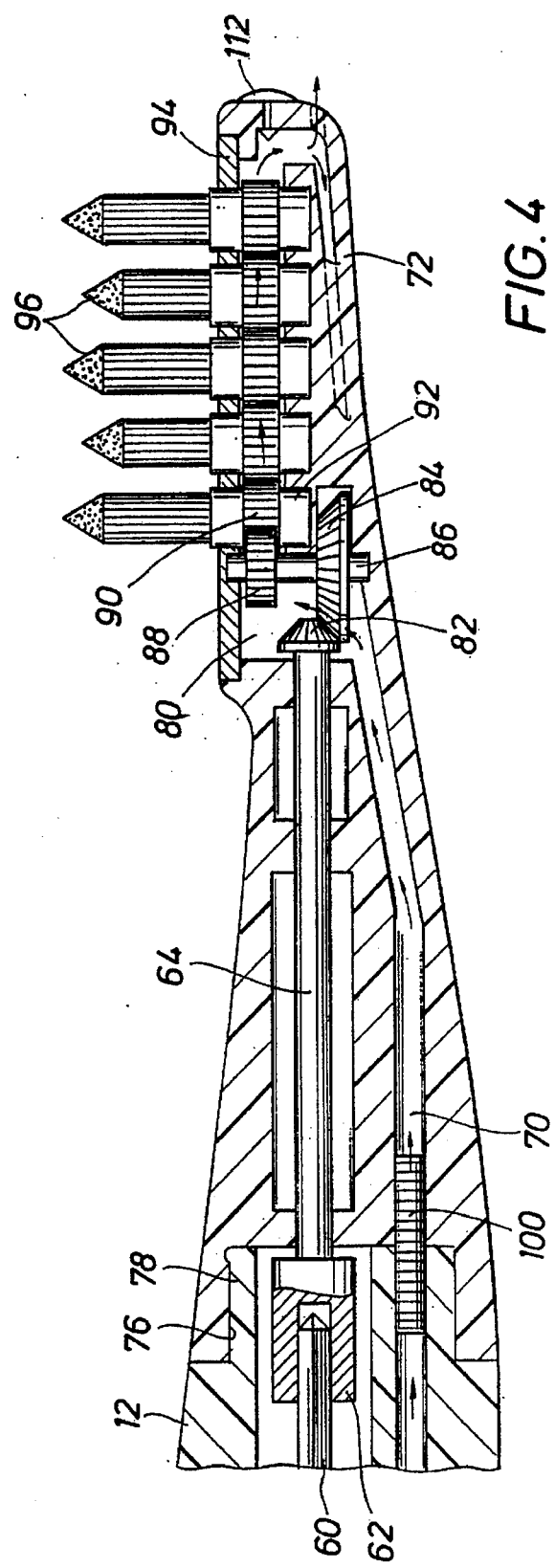

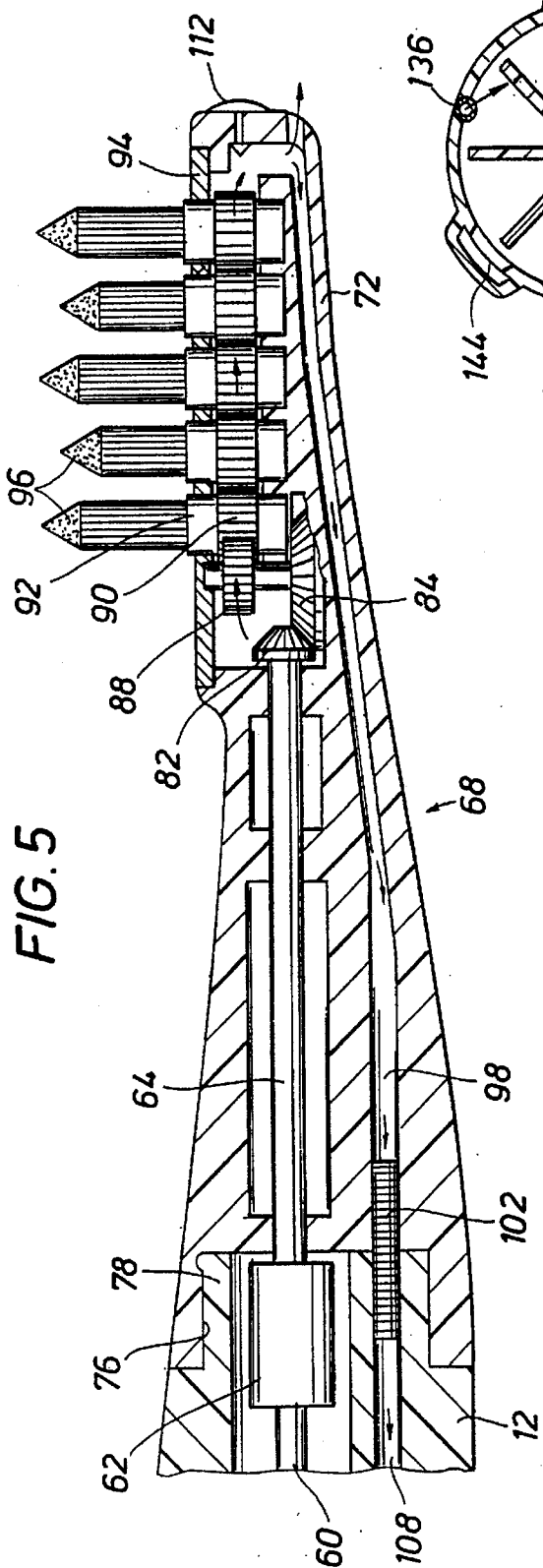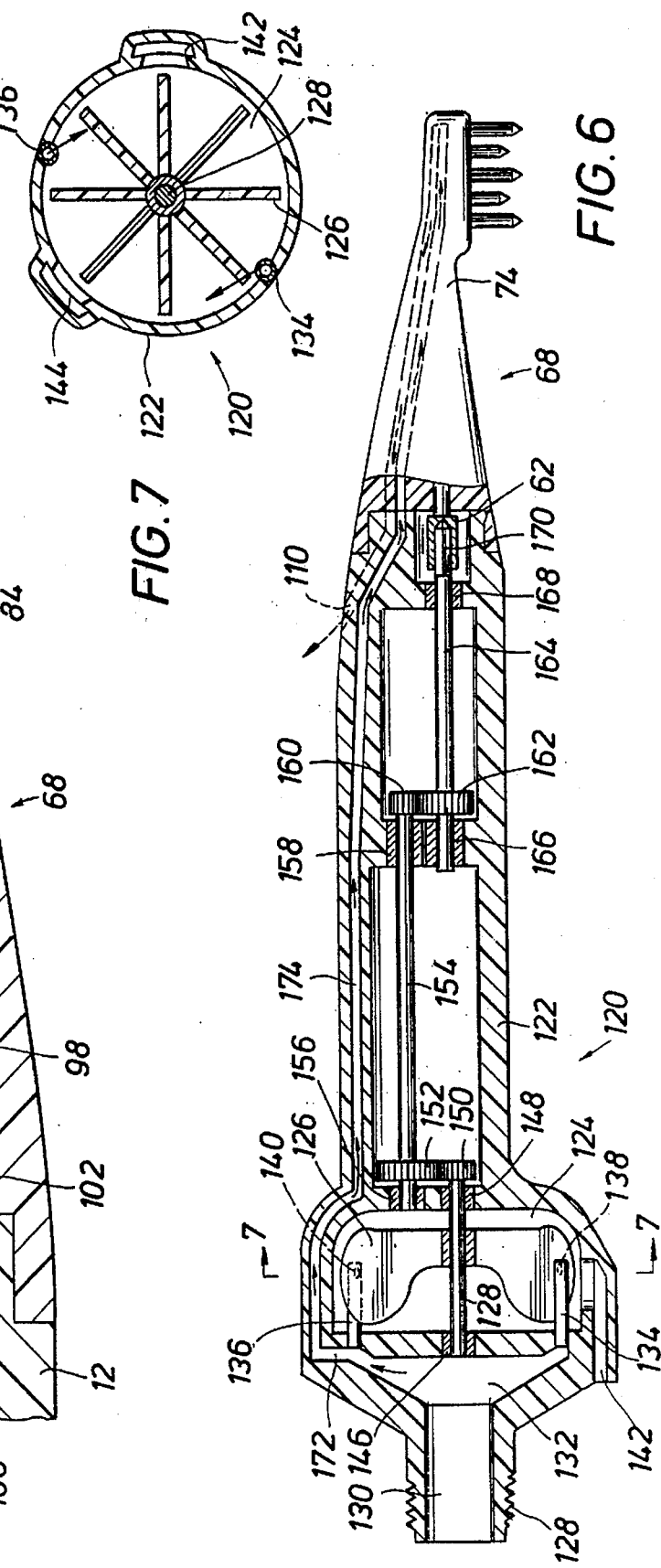

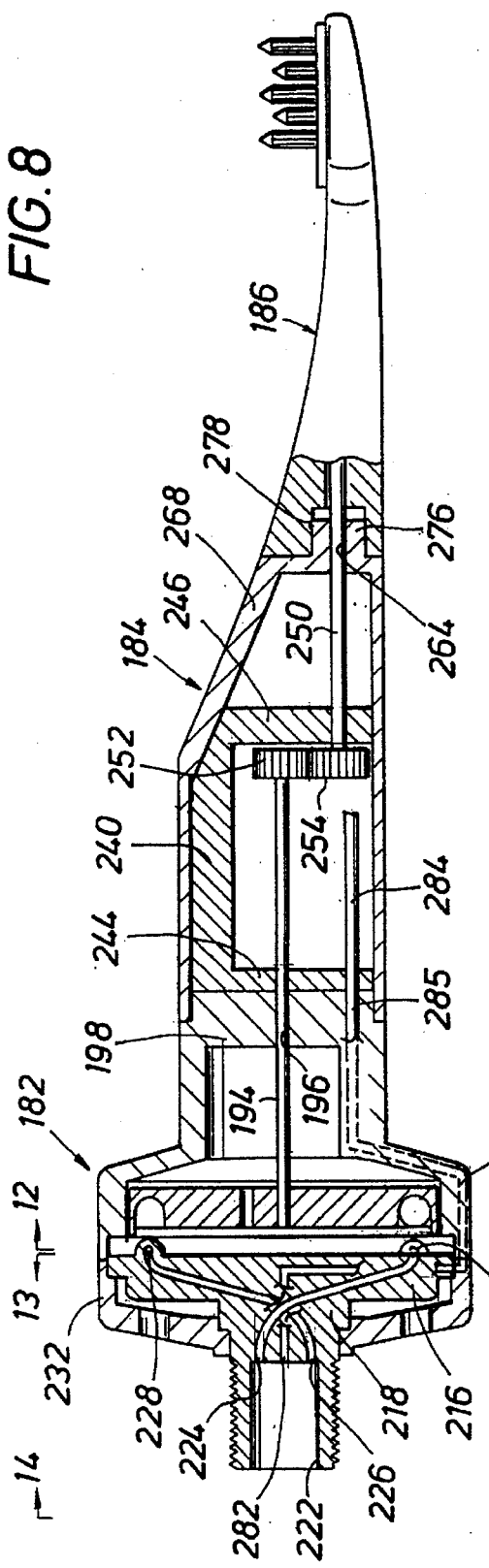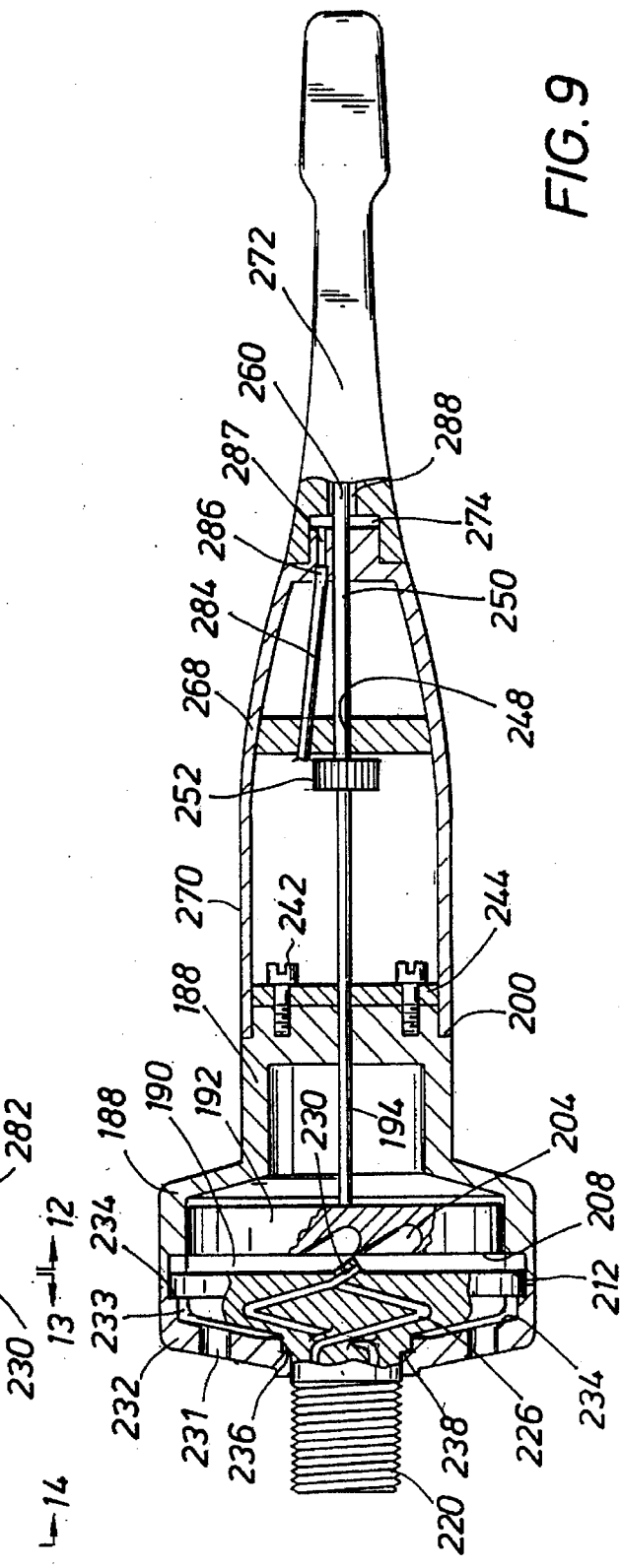

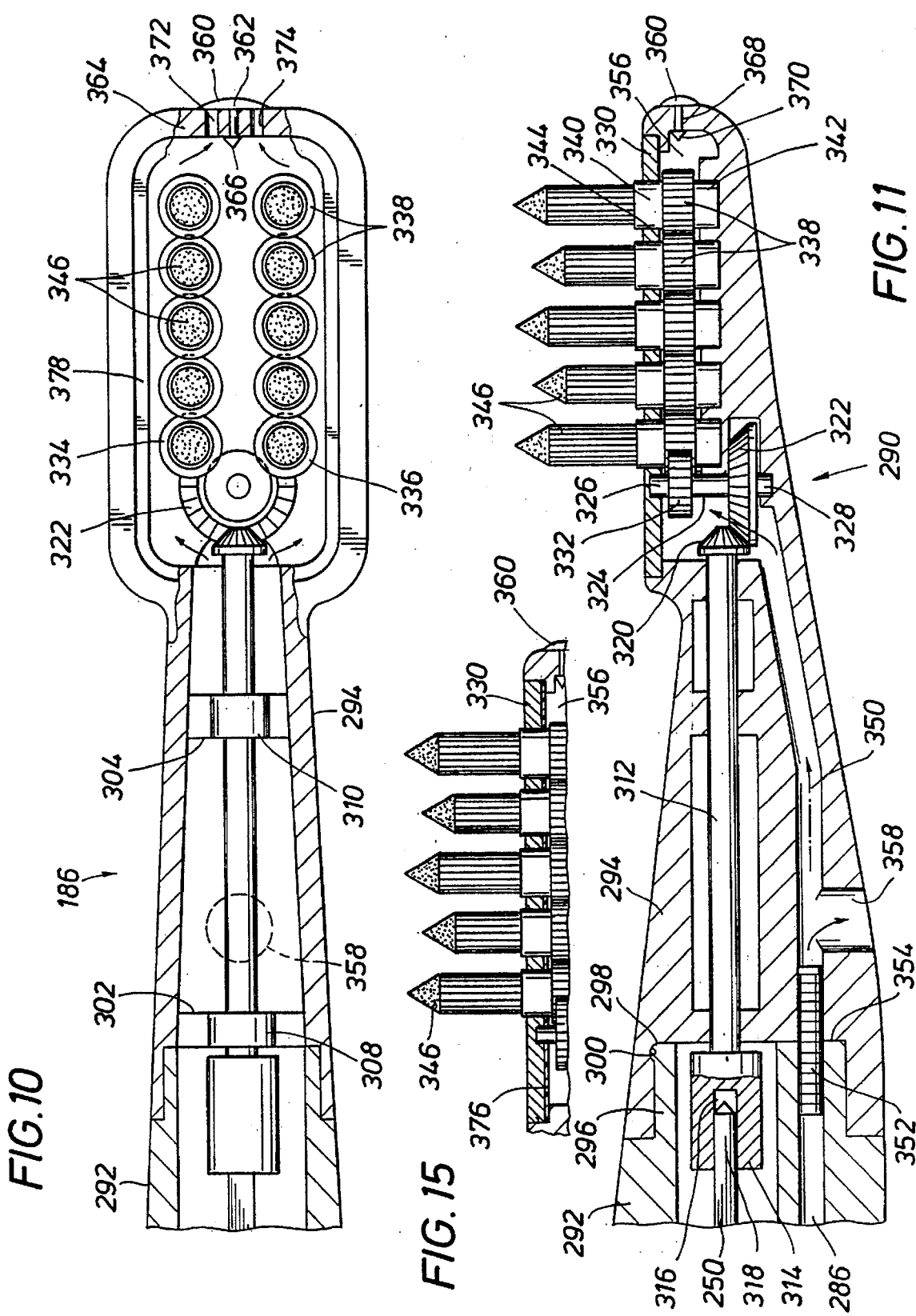

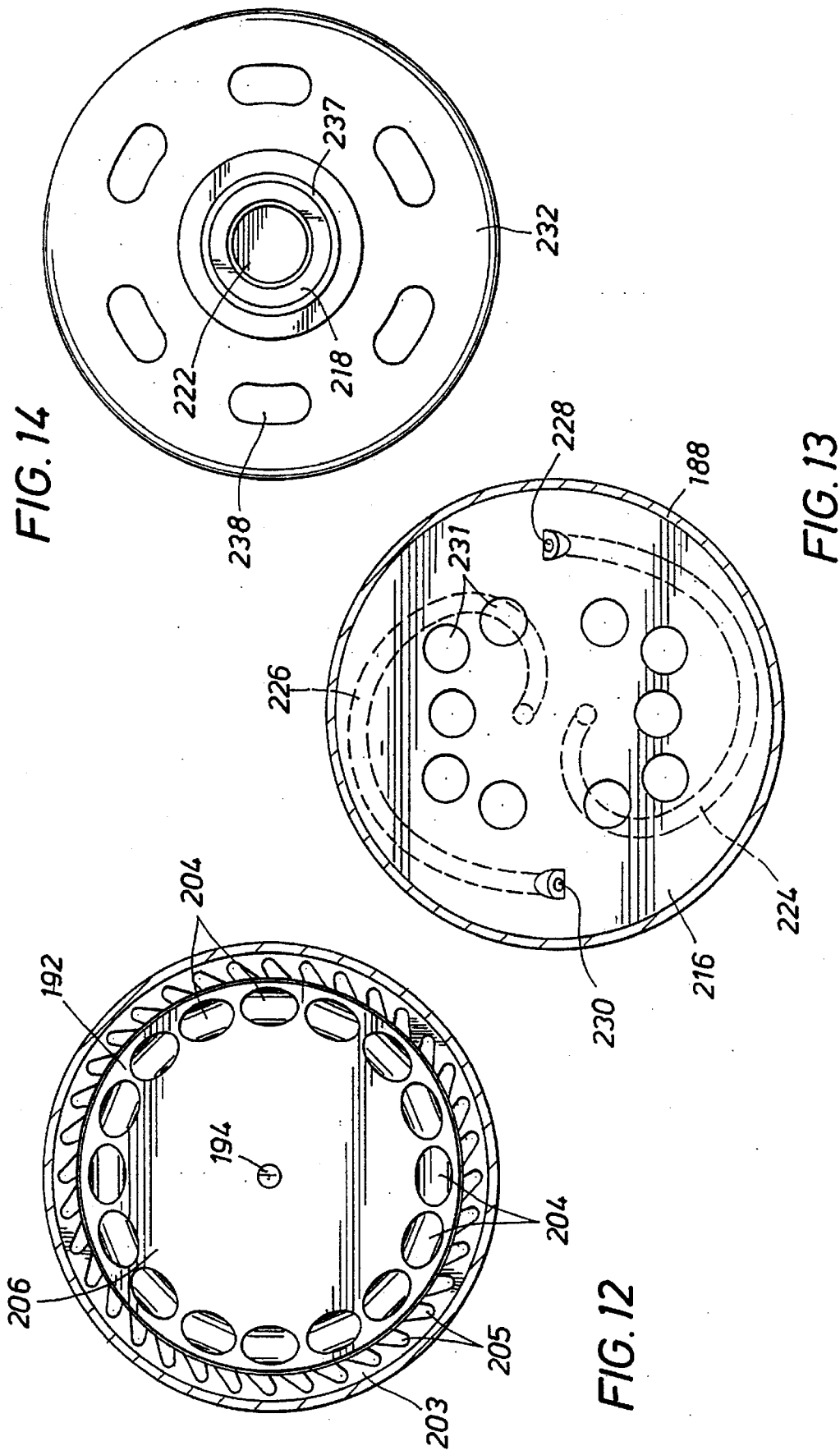

TURBINE POWERED TOOTHBRUSH HAVING GEAR FLUSHING SYSTEM

This is a continuation-in-part of application Ser. No. 08/264,428 filed by Peter T. Manning filed Jun. 22, 1994, now abandoned, and entitled Turbine Powered Toothbrush Having Gear Flushing System.

FIELD OF THE INVENTION

This invention relates generally to powered toothbrushes having tufts of bristles that are rotated by a powered mechanism to accomplish cleaning of human teeth. More particularly, the present invention relates to motor powered toothbrush mechanisms incorporating gearing for transmitting rotary motion of a motor to rotary movement of a plurality of tufts of bristles. Even more specifically, the present invention is directed to a water turbine driven, gear translated power mechanism for rotatably driving the tufts of bristles and including a water supply system for selectively passing water flow through the brush head of the device for flushing the gear train of the toothbrush mechanism for effective removal of dentifrice particulate and other debris that might cause fouling of the gear train or for controllably providing a flow of water from the brush head and into the oral cavity of the user as desired.

BACKGROUND OF THE INVENTION

It is well known that toothbrushing on a regular basis is necessary for maintenance of a condition of effective oral hygiene. Various types of toothbrushes have been employed for many years to accomplish effective cleaning of the teeth. In recent years it has been determined that effective oral hygiene can be accomplished simply and efficiently through the use of a mechanized toothbrush system whereby bristles of a brush or tufts of bristles are rapidly moved by a suitable power source which may conveniently take the form of a water powered turbine as evidenced by U.S. Pat. No. 1,108,475 and 3,605,154 or may conveniently take the form of an electrically driven mechanism as taught by U.S. Pat. Nos. 2,140,307; 2,215,031; and 4,156,620. Gear mechanisms have also been widely used in powered toothbrush mechanisms for rotating brushes or groups of brushes as indicated by U.S. Pat. Nos. 2,215,031, 2,140,317 and 4,156,620. In some cases the tufts of bristles are driven rotatably and in other cases, rotational oscillation of the tufts of bristles is induced. Further, turbine powered, gear train controlled brush mechanisms have also been widely used in powered brushes of types other than toothbrushes as indicated by U.S. Pat. Nos. 4,513,466; and 4,461,052. Powered brushes having water supply to the brush head have also been widely used in toothbrushes and in brushes that have been designed for other purposes.

Where powered toothbrushes are employed which incorporate gear mechanisms for inducing tooth cleaning motion for tufts of bristles, the brush head typically incorporates a number of small gears. Because dentifrice typically contains abrasive particulate and since food debris is removed from the teeth and other portions of the oral cavity during tooth cleaning and becomes entrained in the dentifrice/water/oral fluid composition, the small gears of the brush head often become fouled and stall or stop functioning completely such that disassembly and cleaning or replacement of the brush drive mechanisms becomes necessary. It is desirable, therefore, to provide a system for effectively preventing fouling of the gears during toothbrushing activities and insuring that upon completion of tooth cleaning activities it will not be necessary to spend additional time and effort in cleaning the toothbrush mechanism itself. Even under circumstances where the brush head gearing is sealed and gear fouling is not a problem it may be desirable to provide for discharge of water from the brush head into the oral cavity of the user or for other desired purposes.

SUMMARY OF THE INVENTION

It is a principle feature of the present invention to provide a novel water turbine motor operated gear driven toothbrush mechanism having a facility for selectively conducting a flow of water through the gear train of the toothbrushing mechanism in order to insure removal of any dentifrice particulate or other debris which might otherwise foul or degrade the gear train mechanism.

It is also a feature of the present invention to provide a motor powered toothbrushing mechanism having a water supply causing water flow to be conducted through the brush head for controlled discharge into the oral cavity of the user during tooth cleaning activities or for other desired purposes.

It is an even further feature of the present invention to conduct a flow of the turbine discharge or the flow of an internal water supply circuit through the gear train of the toothbrushing mechanism in order to insure continuous removal of any dentifrice particulate or other debris which might otherwise foul the gear train mechanism.

It is another feature of this invention to provide a novel turbine powered toothbrush mechanism incorporating a manually operated water supply control that will enable the user to control the speed and power of the toothbrush mechanism as well as to control the volume of water being conducted through the gear train of the toothbrush head for cleaning of the gear drive mechanism thereof.

It is an even further feature of this invention to provide a novel powered toothbrush mechanism which may be electrically powered if desired and may incorporate a water supply system for the purpose of accomplishing continuous flushing of dentifrice particulate and other contaminants from the gear train of the toothbrush mechanism while in function.

It is also a feature of this invention to provide a novel mechanized gear translated powered toothbrush mechanism which, is driven by water flow and which, separate from the water flow drive thereof, provides for circulation of clean water through the gear system of the toothbrush mechanism to thereby accomplish continuous cleaning of the gear train during toothbrushing activity.

It is an even further feature of this invention to provide a novel turbine powered toothbrush mechanism including control valve such as a pressure energized control valve for the purpose of permitting the user to selectively inject water from the gear cleaning circulation system into the mouth of the user as desired for toothbrushing activity.

Briefly, the present invention is directed to a powered toothbrush mechanism which is preferably driven by a water powered turbine motor but which may be driven by any other suitable power energized mechanism without departing from the spirit and scope of the present invention.

The preferred turbine powered toothbrush mechanism incorporates a rotatable shaft mounted turbine motor which is driven by flowing water flowing from a suitable water source, such as a water circuit for a shower bath within which the person may be located. If desired, the water supplied for the turbine motor may be continuously open to the water circuit of the shower bath, thereby enabling water pressure control to be accomplished by the water flow control of the shower bath. In the alternative, the housing of the toothbrush mechanism may incorporate a manually operable control valve, thus enabling the user to control the flow of water, including its velocity by manual manipulation of the control valve to thus control operation of the turbine motor.

The turbine motor may be provided with a plurality of water inlets into the turbine impeller cavity which are angularly arranged in relation to the turbine impeller blades to enhance the transmission of the force of water pressure to the blades in sequential manner so as to thereby enhance the effective driving power of the turbine motor.

Interconnection between the drive shaft of the turbine motor and the tufts of bristles that are rotatably supported within the brush head is accomplished by means of a gear train that may include bevel gears and pinion gears as well as any other suitable gear drive system. Each of the tufts of bristles is driven by separate pinion gears that are oriented in serial fashion so that each gear accomplishes driving rotation of a next gear in series. For the reason that the bevel gears and pinion gears may become fouled with particulate of the dentifrice that is used and may be fouled with any other debris that may be present in the oral cavity during toothbrushing activities, the toothbrush mechanism incorporates a water flushing circuit for conducting clean water through the brush head for continuous cleaning of the gear train. The water flushing circuit may include a return conduit which returns the flushing water to a suitable discharge that is positioned so as not to inject water into the oral cavity of the user during toothbrushing activities.

In the brush head, and in communication with the water flushing circuit, may be provided a simple water control valve which is normally closed but which may be opened to permit controlled injection of a desired quantity of water from the water flushing circuit into the oral cavity of the user. This injection control valve may, if desired, be a simple normally closed check valve which is opened responsive to sensing a predetermined water pressure. The water pressure in the water flushing circuit may be increased to a level to accomplish opening of the injection control valve simply by placing the user's finger over the water flushing discharge outlet so that the pressure controlled valve opens and emits water into the oral cavity. By removing the user's finger from the water flushing discharge outlet, the water pressure will decrease and the injection control valve will automatically close, thereby ceasing admission of water into the oral cavity.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

IN THE DRAWINGS

FIG. 1 is a sectional view of a turbine powered, valve controlled toothbrush mechanism incorporating a bristle tuft gear drive mechanism and incorporating a gear flushing system in accordance with the teaching of the present invention.

FIG. 2 is a fragmentary sectional view of the turbine energized toothbrush mechanism of FIG. 1 illustrating the control valve portion thereof in detail.

FIG. 3 is a sectional view of the cleaning head portion of the toothbrush mechanism of FIGS. 1 and 2 and which includes flow arrows representing the flow of gear flushing water to the brush head in accordance with the teachings of this invention.

FIG. 4 is a sectional view of the toothbrush head structure, taken along line 4—4 of FIG. 3, and illustrating the inlet passage system for conducting flushing water to the brush head and further showing a portion of the water flushing discharge from the brush head.

FIG. 5 is a sectional view taken along line 5—5 of FIG. 4 and illustrating the water flow circuitry for conducting flushing water from the brush head to the discharge outlet of the toothbrush mechanism.

FIG. 6 is a sectional view of an alternative embodiment of the present invention which incorporates a gear flushing system in accordance with the teachings of this invention and which incorporates a valveless water drive turbine mechanism.

FIG. 7 is a sectional view taken along line 7—7 of FIG. 6 and which illustrates angularly controlled application of water injection by means of staggered inlet jets to the turbine rotor for maximum power enhancement thereof.

FIG. 8 is a sectional view of an alternative embodiment of the present invention incorporating a water turbine drive mechanism for bristle operation and incorporating a manually controlled gear flushing system according to the teachings of the present invention.

FIG. 9 is another sectional view of the turbine powered tooth brush mechanism of FIG. 8.

FIG. 10 is an enlarged sectional view showing the turbine driven brush head mechanism of FIGS. 8 and 9.

FIG. 11 is another sectional view taken through the brush head mechanism of FIG. 10 and showing the gear drive and gear flushing system thereof in detail.

FIG. 12 is a sectional view taken along line 12—12 of FIG. 8 and showing the turbine impeller of the turbine drive mechanism in elevation.

FIG. 13 is a sectional view taken along line 13—13 of FIG. 8 and showing the stator of the turbine drive mechanism in elevation.

FIG. 14 is an end view taken along line 14—14 of FIG. 8 and showing the vented turbine housing structure in detail.

FIG. 15 is a sectional view of a sealed brush head representing an alternative embodiment of this invention.

DETAILED DESCRIPTION OF PREFERRED EMBODIMENT

Referring now to the drawings and first to FIGS. 1 and 2 a turbine powered toothbrush mechanism is illustrated generally at 10 which incorporates a housing structure 12 defining a turbine impeller cavity 14. The housing also defines an inlet section 16 which is adapted such as by threaded section 18 for attachment of the powered toothbrush mechanism to a suitable water supply conduit such as a flexible hose. The flexible hose will extend from a suitable water supply such as a shower bath water supply circuit. The inlet portion of the housing defines an inlet passage 20 which is in communication with a valve cavity 22 having a water control valve positioned therein. Although the drawings illustrate a valve of specific construction, such should not be taken as limiting the spirit and scope of the present invention. Any suitable water control valve may be employed in place of the valve shown without departing from the spirit and scope of the present invention. As shown, the valve mechanism incorporates a valve body structure 24 which is received by an internally threaded external portion 26 of the valve cavity 22. The valve body defines a circular valve seat 28 which is positioned for contact by a resilient sealing member 30 of a valve plunger 32 for terminating the flow of water from the inlet passage 20 into the annular flow passage 34 downstream of the valve seat. The plunger-type valve element 32 is urged toward its closed position by means of a compression spring 36. An outer portion 38 of the valve element 32 extends from the valve cavity through a suitable packing 40 supported by the valve body 24 and is positioned for engagement by a valve operating handle 42 which is connected by pivot 44 to the body structure 12. The handle 42 is manipulated to open the control valve and thus operate the turbine drive motor of the toothbrush mechanism.

Within the turbine impeller cavity 14 is located a turbine rotor 46 which is supported for rotation by a shaft 48 having one end thereof rotatably seated within a bushing 50 provided internally of the body structure. The rotor shaft 48 is also journalled for rotation by a bushing 52 that is positioned within the body structure at the opposite side of the rotor cavity 14. The various blades of the rotor are positioned to receive the force of water being injected into the rotor cavity from one or more rotor discharge nozzles 54 that are in communication with a valve outlet passage 56. In this regard, reference may be had to FIG. 7 which illustrates water jet positioning in relation to the turbine rotor blades for power enhancement. A discharge passage 58 is disposed in communication with the rotor chamber 14 and permits the discharge of water from the rotor chamber following its use in driving the rotor 46. Thus, when the valve plunger 32 is unseated by the control lever 42, as shown in FIG. 2, water under pressure flows through the inlet passage 20 and across the valve seat and through the passage 56 into the rotor chamber where it bears against the blades of the turbine rotor, thus imparting rotation to the rotor and to the shaft 48 to which the central portion of the rotor is fixed. The elongate rotor shaft 48 defines a non-circular drive extremity 60 which is received by a mating drive socket 62 and which imparts rotation to a brush head drive shaft 64. The brush head structure will be described in detail hereinbelow in connection with FIGS. 3–5.

The body structure 12 of the toothbrush mechanism is formed to define a gear flushing passage 66 which is in communication with the impeller chamber supply passage 56 and which conducts a flow of flushing water through the body structure 12 to a brush head assembly shown generally at 68. The flushing water supply passage 66, when the brush head assembly 68 is in assembly with the body structure as shown in FIG. 1, is in communication with a flushing water inlet portion 70 of a flushing water circuit that is defined within the brush head structure. Alternatively, the flushing water circuit may be located partially externally of the housing if desired. The brush head assembly 68 defines a brush head 72 having an elongate shank 74 which in turn defines an internal attachment socket 76 adapted to receive a connector projection 78 of the body structure 12 for releasably securing the brush head structure to the body 12. The brush head 72 forms an internal gear chamber 80 within which is located a bevel gear 82 provided at a terminus of the brush head drive shaft 64. Bevel gear 82 is coupled in driving relation with another bevel gear 84 which is rotatably supported by a shaft 86 that is disposed in substantially normal relation with the shaft 64 and is rotatably positioned within the gear chamber 80. A pinion gear 88 fixed to the shaft 86 is disposed in driving relation with a pinion gear 90 having a stub shaft 92 that is also positioned for rotation within the brush head. A support cover structure 94 is secured to the brush head 72 and defines a plurality of openings through which the stub gears project. Each of the stub gears is provided with a tuft 96 of bristles which are rotated as the stub gears are rotated.

As is evident from FIG. 3, the brush head contains two spaced rows of gear driven bristle tufts with drive pinion gear 88 being disposed in driving relation with the gears of each row. Thus, the single gear 88 accomplishes driving rotation of both rows of interrelated pinion gears.

As mentioned above the various gears of the gear train for imparting rotary movement to the bristle tufts may become fouled with dentifrice and other particulate matter through use of the apparatus in the oral cavity. This fact exists because, to permit freedom of gear, gear shaft and tuft rotation the gears are not sealed. It is desirable, therefore, to provide a suitable means for accomplishing continuous flushing of the gear train with clean water as the toothbrushing operation is in progress. One suitable means for accomplishing this feature may conveniently take the form shown particularly in FIGS. 3–5. The clean water inlet passage 70 and a water discharge passage 98 are each provided with transition conduit members 100 and 102 respectively which function to bridge the releasable connection joint between the brush head assembly and the body structure 12. The transition conduit members provide sufficient sealing capability that water leakage at the joint is prevented. It should be born in mind that other types of joint seals may also be employed for this purpose. The clean water supply passage 70 opens into the gear chamber 80 such that its flow impinges directly upon the bevel gears 82 and 84 and then flows centrally through the gear cavity as shown by the flow arrows. At the terminal end wall 104 of the brush head the flushing water flow, having picked up any particulate that might have been present on the various bevel gears and pinion gears, enters the collection portion 106 of the return passage 98. Thence, the slightly contaminated water flowing from the gear chamber 80, after passing through transition sleeve 102 as shown in FIG. 5, flows through return passage section 108 of the body structure 12 and, as shown in FIG. 6, exits via a discharge outlet 110. It should also be born in mind that the positive water pressure of water flowing through the gear chamber of the brush head may form minute water leakage from the gear chamber along each of the rotating tuft support shafts. This feature helps minimize fouling of the gears because most of the particulate present around the gear shafts will be prevented from entering the gear chamber.

It will be appropriate from time to time to controllably inject a quantity of water into the oral cavity for the purpose of rinsing during the toothbrushing activity. One suitable means for accomplishing this feature may conveniently take the form of a simple water injection control valve 112 which may be composed of a flexible sealing material such as rubber or any one of a number of suitable elastomeric materials. The water injection control valve is secured in place by an integral projection 114 that extends through a hole 116 in the end wall of the gear chamber and which is provided with an integral retainer button 118. A peripheral portion 120 of the flexible valve is disposed to overly a water injection aperture 122 which is defined in the end wall 104. The aperture 122 is normally closed by the flexible outer peripheral portion 120 of the valve 112 but is displaced from its closed position upon a predetermined increase in water pressure within the gear chamber 80. This increase in pressure is controllably achieved by the user simply by placing a finger over the exit port 110 of the discharge or return passage 98. The increase in water pressure within the gear chamber 80 simply unseats the sealing portion 120 of the valve 112 thereby allowing injection of water through the port 122 past the valve and into the oral cavity. As soon as the user's finger is removed from the outlet port 110, the water pressure within the chamber 80 decreases below the valve opening pressure level and thus sealing portion 120 of the valve 110 again prevents flow of water into the oral cavity. Although an integral resilient valve is shown to accomplish this purpose, any other suitable type of valve that is opened responsive to an increase of pressure within the gear chamber 80 may be suitable for this intended purpose. Additionally, other types of manually operated valves may also be employed instead of the pressure responsive valve 112.

Referring now to FIG. 6, an alternative embodiment of the present invention is illustrated generally at 120 which includes a body structure 122 forming a turbine impeller chamber 124 within which is rotatably positioned a turbine rotor 126. The turbine rotor is fixed to a rotatable turbine shaft 128. The housing structure 122 defines an externally threaded water inlet projection 128 forming a water inlet passage 130 in communication with the impeller chamber 124. A suitable water supply, not shown, which will typically be in the form of an elongate flexible water supply conduit, will be connected to the externally threaded projection 128. It should be noted that the powered toothbrush mechanism 120 does not incorporate a water control valve for controlling the pressure of water flowing through the inlet passage 130. Thus, water pressure control is achieved by means of any suitable remotely located water supply valve to control the pressure and velocity of water flow through the flexible water supply conduit representing the water supply source.

Immediately downstream of the water inlet passage 130 the housing structure 122 defines a water inlet chamber 132 being disposed in communication with a pair of impeller jet conduits 134 and 136, each forming water jet openings 138 and 140 respectively. The water jet openings, as illustrated in the cross-sectional view of FIG. 7, are oriented with respect to the various blades of the impeller 126 that substantially continuous water energized power is delivered by the jets to the impeller blade, to enhance the power delivery of the impeller to the impeller shaft and gear train which will be described hereinbelow. The water jets emanating from the water jet openings are staggered in relation to the spacing of the tips of the rotor blades and are oriented at differing angles with respect to the circular path of the rotor blades such that at any given time, in the rotational cycle of the impeller, water induced force is being transmitted to at least two blades of the impeller so that substantially continuous force application will be delivered from the impeller to the impeller shaft and gear train. By staggering the water jets in this manner, maximum water induced force is being delivered to a rotor blade at the same time that minimum water induced force is being delivered to an adjacent blade. This feature develops maximum turbine force output for brush rotation. This substantially constant water induced energy input will cause the toothbrush mechanism to have a substantially constant power delivery level. The power output of the turbine motor is substantially increased by this water jet orientation.

The housing structure 122 of the toothbrush mechanism also defines discharge passages 142 and 144, one being associated with each of the impeller driving water jets. These exhaust passages permit discharge of water from the impeller chamber 124 after the energy of the water has been transmitted to the impeller.

The impeller shaft 128 is journalled for rotation by means of bushings 146 and 148 which are supported within the housing structure 122. At its inner extremity the impeller shaft supports a pinion gear 150 having its teeth in driving relation with the teeth of a driven pinion gear 152 supported by a gear train shaft 154. The shaft 154 is journalled by bushings 156 and 158 within the housing and is provided with a pinion gear 160 at the inner extremity thereof. Pinion gear 160 is disposed in driving relation with a pinion gear 162 supported by a gear shaft 164 that is journalled for rotation within the housing by means of bushings 166 and 168. At its inner extremity, gear shaft 164 defines a noncircular drive portion 170 which is received by the drive socket 62 of the brush head assembly shown generally at 68. The brush head assembly 68 may conveniently be of the same construction and operation as described above in connection with FIGS. 3–5; consequently, the structural components are indicated by like reference numerals.

A flushing water supply conduit 172, formed in part by an internal water supply passage 174 is disposed in communication with the water inlet chamber 132 and serves to provide a continuous supply of clean water to the water inlet passage 70 of the toothbrush head 68. Since the conduit 172 and passage 174 are not valved in any manner, as long as water pressure exists within the inlet chamber 132 a flow of flushing water is continually directed to and through the gear system of the toothbrush head to provide for efficient removal of any dentifrice particulate or other particulate debris which may be present within the gear chamber 80 of the toothbrush head. Additionally, placement of the finger of the user over the water outlet opening 110 will increase the pressure within the gear chamber 80 and will thereby induce opening of the pressure operated valve 112 to controllably inject water into the oral cavity of the user.

Referring now to FIGS. 8–14 an alternative embodiment of the present invention is illustrated generally at 180 which represent the preferred embodiment of the present invention and which incorporates a turbine drive section shown generally at 182 a brush drive section shown generally at 184 and a brush head section shown generally at 186. The turbine drive section 182 incorporates a turbine housing 188 defining a turbine chamber 190 within which is mounted a turbine rotor 192 which is supported for rotation by a turbine shaft 194 being journalled for rotation within a shaft passage 196 of a housing wall 198. The wall 198 of the turbine housing 188 is preferably formed integrally with the turbine housing and at its outer periphery defines a circular recess 200 which is adapted to receive the housing structure 202 of the brush drive section 184 in assembly therewith.

The rotor or impeller 192 defines a multiplicity of impeller drive pockets 204 which are inclined with respect to a rear planar surface 206 of the impeller as is evident from FIGS. 9 and 12 and which are arranged about the outer peripheral portion of the impeller so as to receive jets of water from the jet openings of the stator of the turbine drive mechanism in a manner to be discussed herein below.

The turbine housing 188 defines a stator seat 212 which receives the outer peripheral flange portion 214 of a water supply stator 216. The stator includes a generally plate-like outer peripheral portion from which projects an integral, centrally located water supply connection 218 having an externally threaded section 220 which is adapted to receive a conventional water supply coupling defining a main water supply inlet 222. The water supply inlet receives water from a pressurized source, such as the valve controlled water supply of a shower bath. The user will be able to effectively control the pressure of water inlet to the toothbrush mechanism simply by adjusting the water supply valve. It is not necessary therefore that the toothbrush mechanism be provided with its own water pressure control valve. From the water supply inlet extends a pair of branch impeller supply passages 224 and 226 which extend through the plate portion of the stator and terminate at respective impeller jets 228 and 230 respectively which are oriented to direct jets of water at supply pressure into the angulated impeller pockets 204 as is clearly evident from FIGS. 9 and 13. The turbine water supply passages 224 and 226 are of helical-like, gently curved configuration to ensure against the development of back-pressure and turbulence as the pressurized water is conducted from the water inlet to the water jets. The stator is secured in place by a turbine housing closure and retainer 232 having an internal peripheral receptacle 234 which receives and retains the outer peripheral portion of the stator 216 and cooperates therewith to define a turbine exhaust chamber that receives turbine exhaust water from a plurality of exhaust apertures 231 which are shown in FIG. 13. The closure 232 further defines a centrally located stator coupler receptacle 236 which receives an outwardly directed shoulder portion 238 of the stator coupler 218 and thus securely locks the stator against movement within the turbine chamber of the turbine housing structure.

As water is directed into the main water inlet 222 under the pressure control of a remotely located valve in the water supply, the water at supply pressure flows through the helically curved branch water supply passages 224 and 226 and emerges as water jets at the jet openings 228 and 230. The stator also defines a plurality of turbine exhaust openings 231 through which water flows from the turbine chamber 190 into an exhaust chamber 233. The turbine exhaust is then directed from the turbine housing through a plurality of exhaust openings 238 as shown in FIG. 14 so that the exhaust emerges in a direction substantially opposite the direction of water inlet into inlet opening 222. As the water jets emerge from the jet openings 228 and 230 at high velocity, the water jets are directed at an acute angle of about 20 degrees with respect to the rear planar surface 208 of the impeller and are thus directed into the impeller pockets 204 which, because of their angular orientation, impart rotary force to the impeller 192 thus rotating the impeller and the impeller shaft 194. The rotary force of the impeller acting through the rotary shaft 194 is utilized to drive a gear mechanism for achieving toothbrush operation.

Within the turbine housing 188 there is provided an annular jet reflector structure 203, which may be molded or otherwise formed within the housing or may be a separate circular structure that is fixed within the housing. The jet reflector defines a multiplicity of inclined water reflector pockets 205 that face radially inwardly and are angulated in much the same manner as the jet pockets. As the water leaves the jets 230 and enters the jet pockets 204 it will tend to "bounce back" from the jet pockets and develop a swirling effect within the turbine chamber and adjacent the rotor. This swirling action can detract from the force that is induced to the turbine rotor 192 by the jetted water because of the turbulence and water swirling that can otherwise occur as the water jets are deflected by the rotor. The reflector pockets are angulated so as to oppose the swirling action of the water and to direct the water swirling water back against the jet pockets of the rotor. In essence the reflector pockets enhance the force transmission of the jetted water against the turbine rotor and thus enhance the water induced power output of the turbine motor. The jet reflector structure, if desired, may be an integral component of the stator element 216 or may be defined by a circular reflector element which is in assembly within the turbine housing.

A gear support body 240 is secured to the housing wall 198 such as by assembly screws 242 extending through an assembly wall 244 of the gear support body and provides support for the turbine impeller shaft 194. The support body 240 defines a transverse support wall 246 having an opening 248 therein which serves as a journal for a rotary brush drive shaft 250. Pinion gears 252 and 254 are fixed to respective extremities of the impeller shaft 194 and the brush drive shaft 250 and are disposed in intermeshing geared relation so that rotation of the impeller shaft imparts driving rotation to the brush drive shaft at a ratio that is determined by the gear teeth of the respective pinion gears. The brush drive section 184 of the turbine driven toothbrush mechanism incorporates a brush drive housing 268 having a connection extremity 270 which is received by the circular peripheral connection recess 200 of the turbine housing 188. The forward end of the brush drive housing defines a passage 268 through which the brush drive shaft 250 extends and which serves as a bearing and alignment support for the rotary shaft.

The brush head section 186 of the turbine powered toothbrush mechanism incorporates a head extension 272 having a connection receptacle 274 which is adapted to receive a connection projection 276 of the brush drive housing 268. A retainer projection 278 of the projection 276 is received by a small internal receptacle to provide for quick release connection of the brush head section 186 to the brush drive section 184. The rotary drive shaft 250 extends into the brush head and establishes a driving arrangement which imparts rotation to the gear driven bristle tufts 280 of the brush head to accomplish toothbrushing activity.

As mentioned above, the turbine housing 188 defines a water supply inlet 222. According to the teachings of the present invention passage means is provided for selectively conducting a supply of water from the water inlet 222 to the brush head for the purpose of discharging water into the mouth of the user or passing water through the brush head for flushing away any debris that might be present within the brush head which might foul the bristle tuft gears or interfere with rotation of the bristle tufts. As shown in FIGS. 8 and 9 a water supply conduit 282 or passage defined in the stator 218 and in the wall structure of the turbine housing and is in communication with the water inlet 222. A water supply conduit 284 is provided having one end 285 thereof received within a passage of the housing wall 198 so that water is enabled to flow directly from the water inlet, around the turbine and through the water supply conduit 284. As shown in FIG. 9 the water supply conduit is provided with its opposite end 286 being received by a passage 287 of the brush drive housing 268 for communication with a brush head water supply passage 288. The brush head passage 288 through which the shaft 260 extends is of larger dimension than the shaft so that an annulus passage is defined which conducts water supply along the shaft 260 and into the gear chamber of the brush head.

With reference now to FIGS. 10 and 11 the brush head section 186 of the water turbine powered toothbrush is shown, with the bristle tuft drive mechanism thereof being shown in detail. The forward portion of a brush drive housing is shown at 292 and is arranged so that the brush head 294 may be releasably assembled to the body by means of a snap fit. As shown in FIG. 11 a forward projecting portion 296 of the brush housing 292 is provided with a small snap fit projection 298 that is receivable within an internal receptacle 300 of the brush head 290 and thus provides a snap fit arrangement so that the brush head can be simply and efficiently assembled and disassembled from the toothbrush body structure.

The brush head is provided with a pair of internal support spiders 302 and 304 having central portions 308 and 310 which define journals to provide rotary support for a brush head drive shaft 312. The drive shaft is in turn provided with a socket head 314 at one end thereof defining an internal noncircular drive receptacle 316 that is adapted to receive a noncircular drive end of the rotary brush drive shaft 250 in releasable assembly therewith. As the brush head 294 is removed from the body structure 292 of the brush assembly the drive shaft 250 will remain as shown in FIG. 11 and the socket head 314 will be removed along with the brush head. At the end opposite the socket head 314 the rotary shaft 312 is provided with a bevel gear 320 which is in driving engagement with a larger bevel gear 322 which is mounted for rotation within the brush head by a gear shaft 324 having its respective extremities 326 and 328 journalled for rotation within internal blind journals of the brush head and a brush head cover plate 330. The rotary shaft 324 is also provided with pinion gear 332 having driving inner engagement with the first gears 334 and 336 of a bristle tuft gear train. Each of a plurality of bristle tuft gears such as shown at 338 in FIG. 11 is provided with upper and lower cylindrical portions 340 and 342 which are journalled for rotation within blind journals of the brush head and journals defined by a plurality of apertures 344 of the cover plate 330. Thus, as the bevel gear 320 is rotated it imparts driving rotation to bevel gear 322 and pinion gear 322. The pinion gear then imparts driving rotation to the first two pinion gear sections of bristle tuft gears 338 thus simultaneously rotating two rows of bristle tuft gears and the toothbrush bristles 346 which are supported by the individual bristle tuft gear elements.

It is a feature of the present invention to provide a flushing system for the gears of the brush head which permits selective flushing as needed for gear cleaning and also permits selective injection of water into the mouth of the user from the brush head. As shown particularly in FIG. 11 the toothbrush housing is provided with a water supply channel 286 which is in communication with a water supply channel 350 of the brush head via a bridge tube 352 which bridges the joint 354 between the brush head and housing. The water supply passage 350 of the brush head is in communication with a gear chamber 356 within which the bevel gears the drive pinion gear and the tuft gears are located. The brush head is also provided with a vent opening 358 which is located intermediate the length of the brush head and at a location near the connection joint of the brush head to the body 292. The vent opening is of significantly larger cross-sectional dimension as compared to the cross-sectional dimension of the water supply passage 350 thus causing water to be normally vented to the surrounding environment as it passes into the water supply passage 350 from the brush housing passage 348. Thus, there is normally no flow through the water supply passage 350 into the gear chamber 356 because the water flow is vented through the water vent opening 358. In the event it is desired to inject water from the brush head into the mouth of the user or to cause water flow through the gear chamber 356 such as for the purpose of flushing away any debris that might be present within the gear chamber, such can be accomplished through the provision of a water outlet control valve 360. This valve, as shown in FIGS. 10 and 11 may conveniently take the form of a unidirectional check valve having a valve body portion 362 which is secured to an end wall 364 of the brush head by means of a valve retainer 366. The valve retainer may be formed integrally with the valve and may be composed of resilient material such as rubber or a rubber-like polymer. The retainer as shown in FIGS. 10 and 11 extends through a retainer passage 368 and is secured in place by a flexible retainer button 370. The valve body 362 overlies a pair of valve outlet openings 372 and 374 which are normally closed by the valve body 362 when the gear chamber 356 is under normal operating pressure. When the water pressure within the gear chamber is increased upon closure of the vent opening 358 such as by the user's finger the valve 360 will be forced open by the flowing water thereby allowing water flow from the chamber 356 through the passages 372 and 374 for injection into the user's mouth or for selective flushing of the gear chamber 356.

During operation of the toothbrush in the presence of an abrasive medium such as conventional dentifrice a small amount of the dentifrice abrasive can enter the chamber 356 where it may constitute fouling for the various gears that are present within the gear chamber. Ordinarily the fit between the rotating brush gear journals 340 and the bristle tuft openings 344 does not permit a positive seal to be developed so that water can enter the gear chamber along the rotating bristle tuft gears and enter the chamber 356. This small amount of particulate or other debris from the dentifrice can be efficiently flushed from the gear chamber simply by closing the water supply vent opening 358 simply by placing the user's finger over it and causing sufficient pressure increase within the chamber 356 that the valve 360 will open. At the conclusion of each toothbrushing session therefore it is wise to close the vent opening in this manner and to flush the gear chamber so that any debris present therein will be flushed through the openings 372 and 374.

In the event it is desirable to insure a positive seal between the rotatable bristle tuft elements and the closure plate 330 an alternative embodiment may be provided as shown in FIG. 15. As shown, a resilient sealing plate 376 may be provided having its edge portions seated against the internal seat surfaces 378 of the brush head and secured in position by the closure plate 330. The sealing plate 376 will have opening formed therein corresponding with the closure plate opening through which the rotatable gear tuft elements project. The openings of the resilient sealing plate may be slightly smaller than the tuft element openings of the plate 330 thereby enabling the development of a positive seal to prevent invasion of particulate material into the gear chamber 356. Since no particulate material can enter the gear chamber due to the presence of the sealing plate, the water supply passage 350 will be utilized only for causing controlled injection of water into the mouth of the user or injection from the brush head as desired.

In view of the foregoing, it is evident that the present invention is one well adapted to attain all of the objects and features hereinabove set forth, together with other objects and features which are inherent in the apparatus disclosed herein.

As will be readily apparent to those skilled in the art, the present invention may be produced in other specific forms without departing from its spirit or essential characteristics. The present embodiment, is therefore, to be considered as illustrative and not restrictive, the scope of the invention being indicated by the claims rather than by the foregoing description, and all changes which come within the meaning and range of the equivalence of the claims are therefore intended to be embraced therein.

What is claimed is:

1. A water turbine energized, gear driven dental toothbrush adapted for fluid communication with a water supply, said toothbrush comprising:

(a) a housing defining a turbine impeller chamber therein disposed for fluid communication with said water supply, said housing having a wall structure and defining a brush head with an internal gear chamber therein, said wall structure defining a flushing water circuit for fluid communication with said water supply, said flushing water circuit being in fluid communication with said internal gear chamber, said brush head having a plurality of tuft apertures therein, said flushing water circuit having a vent aperture in said head normally venting water from said flushing water circuit, said flushing water circuit having valve means for selectively controlling the flow of water through said flushing water circuit and internal gear chamber for discharge through said tuft apertures to flush away dentifrice particulate and other debris from said tuft apertures;

(b) a turbine impeller being mounted for rotation within said turbine impeller chamber of said housing;

(c) a gear train being connected in driven relation with said turbine impeller and having at least a portion thereof located within said internal gear chamber;

(d) a plurality of stub gears each being a part of said gear train and being located within said internal gear chamber, each of said stub gears having a portion thereof extending through a respective tuft aperture and having a bristle tuft fixed thereto and rotatable thereby; and (e) said flushing water circuit having a flushing water inlet passage being defined in said housing and being in fluid communication with said internal gear chamber and said housing having a water exhaust passage leading to a discharge opening in said brush head and being normally closed by said valve means, said water exhaust passage also being in fluid communication with said internal gear chamber, said valve means being pressure responsive and being opened by increase of water pressure within said internal gear chamber upon selective closure of said vent aperture, said flushing water inlet passage and said water exhaust passage being oriented with respect to said internal gear chamber so as to induce the flow of flushing water from said flushing water inlet passage through said gear chamber and to said water exhaust passage to cause flushing water to come into contact with each of said stub gears to flush away any dentifrice particulate and debris therefrom.

2. The water turbine energized, gear driven dental toothbrush of claim 1, wherein:

(a) said stub gears being pinion gears, each being in driving relation with another of said pinion gears;

(b) a drive pinion gear and a driven bevel gear being rotatably mounted within said internal gear chamber by a shaft, said drive pinion gear having geared connection with at least one of said stub gears;

(c) an elongate drive shaft being mounted for rotation within said housing and being rotatably driven by said rotary drive motor, said elongate drive shaft having a drive bevel gear thereon being connected in driving relation with said driven bevel gear;

(d) said flushing water circuit having a supply passage with a valve therein for controlling the flow of water in said flushing water circuit, said supply passage opening into said internal gear chamber and oriented to direct water from said flushing water circuit onto said drive and driven bevel gears and said stub gears of said gear train to flush away any debris thereon; and (e) said flushing water circuit having a water discharge opening being in fluid communication with said internal gear chamber and being oriented to direct water to flow substantially linearly through said internal gear chamber to transport through said water discharge opening any debris that may be present in said internal gear chamber.

3. The water turbine energized gear driven toothbrush of claim 1, wherein said valve means comprises:

a pressure responsive normally closed check valve element being supported by said brush head and normally closing said discharge opening, said pressure responsive valve element being opened in response to predetermined water pressure acting thereon from within said internal gear chamber for pressure controlled discharge of water from said internal gear chamber.

4. The water turbine energized, gear driven toothbrush of claim 1, wherein:

(a) said turbine impeller having a plurality of jet pockets each having angular orientation; and (b) a stator being immovably located within said impeller chamber of said housing and defining a water inlet circuit for communication with the water supply and defining at least one water jet opening for directing a jet of water at substantially the same angulation as the angulation of said jet pockets and being oriented to direct the jet of water into said jet pockets to impart driving rotation to said turbine impeller.

5. The water turbine energized, gear driven toothbrush of claim 4, further comprising:

a jet reflector being provided within said turbine housing and defining a plurality of internal reflector pockets being oriented to retard water swirling activity within said turbine housing.

6. The water turbine energized, gear driven toothbrush of claim 4, wherein:

said stator having at least one turbine water supply passage extending in generally helical smoothly curved manner from said water supply to said at least one water jet opening.

7. The water turbine energized, gear driven toothbrush of claim 4, wherein:

said stator defining a pair of water jet openings being located adjacent the outer periphery thereof and further defining a pair of turbine water supply passages each extending in generally helical smoothly curved manner from said water supply to respective water jet openings and conducting water at supply pressure to said water jet openings.

8. The water turbine energized, gear driven toothbrush of claim 4, wherein:

(a) said turbine impeller being supported for water jet induced rotation within said impeller chamber and defining a planar surface located in generally normal relation to the axis of rotation thereof; and (b) said at least one water jet opening being a pair of water jet openings each being oriented to direct a jet of water therefrom an acute angular relation with said planar surface.

9. The water turbine energized, gear driven toothbrush of claim 4, wherein:

said housing defining a turbine exhaust chamber and defining a plurality of turbine exhaust openings directing exhaust of water from said turbine in a direction substantially opposite the direction of water inlet into said housing.

10. A water turbine energized, dental toothbrush adapted for fluid communication with a pressure controlled water supply, said toothbrush comprising:

(a) a housing defining a turbine impeller chamber having a water inlet for fluid communication with the pressure controlled water supply and having a brush head defining a gear chamber therein, said head having a plurality of tuft apertures therethrough;

b) a plurality of stub gears being located within said gear chamber of said brush head and having portions thereof extending through said tuft apertures each of said stub gears having a bristle tuft fixed thereto;

(c) a flushing water circuit being defined by said housing having a vent aperture in said housing normally venting water from said flushing water circuit of said housing and further having valve means in said brush head for selectively controlling flow of water through said flushing water circuit for discharge at said brush head; said flushing water circuit having a flushing water inlet hassate being defined in said housing and being in fluid communication with said internal gear chamber and said housing having a water exhaust passage leading to a discharge opening in said brush head and being normally closed by said valve means said water exhaust passage also being in fluid communication with said internal gear chamber, said valve means being pressure responsive and being opened by increase of water pressure within said internal gear chamber upon selective closure of said vent aperture, said flushing water inlet passage and said water exhaust passage being oriented with respect to said internal gear chamber so as to induce the flow of flushing water from said flushing water inlet passage through said gear chamber and to said water exhaust passage to cause flushing water to come into contact with each of said stub gears to flush away any dentifrice particulate and debris therefrom and (d) a turbine impeller being mounted for rotation within said turbine impeller chamber of said housing and having driving relation with said stub gears rotation thereof.

11. The water turbine energized, gear driven dental toothbrush of claim 10, wherein:

(a) said stub gears being pinion gears, each being in driving relation with another of said pinion gears;

(b) a pinion drive gear and a driven bevel gear being rotatably mounted within said gear chamber by a shaft, said drive pinion gear having a geared connection with at least one of said stub gears;

(c) an elongate drive shaft being mounted for rotation within said housing and being rotatably driven by said turbine impeller, said elongate drive shaft having a drive bevel gear thereon being connected in driving relation with said driven bevel gear;

(d) said flushing water circuit having a supply passage opening into said gear chamber and oriented to direct the flow of flushing water on said drive and driven bevel gears and said pinion gears to flush away any debris thereon; and (e) said flushing water circuit having a water discharge opening in said brush head being in fluid communication with said gear chamber and being oriented to direct said flushing water to flow substantially linearly through said gear chamber to transport through said water discharge passage any debris that may be present in said gear chamber.

12. The water turbine energized gear driven toothbrush of claim 10, wherein said valve means comprises:

a pressure responsive normally closed check valve element being supported by said brush head and normally closing said water discharge opening, said pressure responsive valve element being opened in response to predetermined water pressure acting thereon from within said gear chamber for pressure controlled discharge of water from said gear chamber through said water discharge opening.

13. The water turbine energized, gear driven toothbrush of claim 10, wherein:

(a) said turbine impeller chamber is in fluid communication with said water inlet and having said turbine impeller rotatably mounted therein, said turbine impeller having a plurality of jet pockets each having angular orientation; and (b) a stator being immovably located within said turbine impeller chamber and defining a water inlet circuit for communication with the water supply and defining at least one water jet opening for directing a jet of water at substantially the same angulation as the angulation of said jet pockets and being oriented to direct the jet of water into said jet pockets to impart driving rotation to said turbine impeller;

(c) a jet reflector being provided within said turbine impeller chamber and defining a plurality of internal reflector pockets being oriented to retard water swirling activity within said turbine housing.

14. The water turbine energized, gear driven toothbrush of claim 13, wherein:

(a) said stator defining an outer periphery and having a pair of water jet openings being located adjacent said outer periphery and further defining a pair of turbine water supply passages each extending in generally helical smoothly curved manner from said water supply to respective water jet openings and conducting water at supply pressure to said water jets;

(b) said turbine impeller being supported for water jet induced rotation within said impeller chamber and defining a planar surface located in generally normal relation to the axis of rotation thereof; and (c) said at least one water jet opening being a pair of water jet openings each being oriented for directing a jet of water in an acute angular relation with said planar surface.

* * * * *